United States Patent
Holland et al.

(10) Patent No.: US 9,579,533 B2
(45) Date of Patent: Feb. 28, 2017

(54) FLOOR EXERCISE SLIDER

(71) Applicant: PRO PERFORMANCE SPORTS, L.L.C., Carlsbad, CA (US)

(72) Inventors: Allen Keith Holland, Sheffield (GB); Daniel John Wray, Carlsbad, CA (US)

(73) Assignee: PRO PERFORMANCE SPORTS, L.L.C., Carlsbad, CA (US)

(*) Notice: Subject to any disclaimer, the term of this patent is extended or adjusted under 35 U.S.C. 154(b) by 45 days.

(21) Appl. No.: 14/444,597

(22) Filed: Jul. 28, 2014

(65) Prior Publication Data

US 2015/0224356 A1 Aug. 13, 2015

Related U.S. Application Data

(60) Provisional application No. 61/939,553, filed on Feb. 13, 2014.

(51) Int. Cl.

| A63B 22/00 | (2006.01) |
| A47D 13/04 | (2006.01) |
| A61H 3/00 | (2006.01) |
| A63B 23/08 | (2006.01) |
| A63B 23/10 | (2006.01) |
| A63B 5/20 | (2006.01) |
| A61H 15/00 | (2006.01) |
| A63B 21/00 | (2006.01) |
| A63B 69/00 | (2006.01) |

(Continued)

(52) U.S. Cl.
CPC .................. *A63B 5/20* (2013.01); *A61F 7/10* (2013.01); *A61H 15/00* (2013.01); *A63B 21/0004* (2013.01); *A63B 69/00* (2013.01); *A61F 2007/0087* (2013.01); *A61F 2007/108* (2013.01); *A61H 2015/0042* (2013.01); *A61H 2015/0064* (2013.01); *A61H 2201/0153* (2013.01); *A61H 2201/0214* (2013.01); *A61H 2201/0257* (2013.01)

(58) Field of Classification Search
CPC .. A63B 5/00; A63B 5/20; A63B 21/00; A63B 21/0004; A63B 22/00; A63B 22/20; A63B 2022/0092; A63B 69/00; A61F 7/10; A61H 15/00
USPC ..... 482/51, 66–68, 79, 82, 148; 601/19, 131
See application file for complete search history.

(56) References Cited

U.S. PATENT DOCUMENTS

| 5,289,830 A * | 3/1994 | Levine ............... A41D 13/0568 128/846 |
| 5,500,955 A * | 3/1996 | Gongea .............. A63B 71/1225 2/24 |

(Continued)

OTHER PUBLICATIONS

Valslide, lower body exercise tool, www.valslide.com; https://www.youtube.com/watch?v=jgoGsrOKiKY (Jan. 1, 2013).

*Primary Examiner* — Stephen Crow
*Assistant Examiner* — Garrett Atkinson
(74) *Attorney, Agent, or Firm* — Torrey Pines Law Group, PC; Kevin W. Buckley

(57) ABSTRACT

A floor exercise slider may have an attachment device on a side of a frame. A resilient pad is attached to an upper surface of the frame, with the resilient pad having raised blocks separated by grooves. A slide plate may be joined to a bottom surface of the frame. The raised blocks may be evenly spaced apart laterally and/or longitudinally by the grooves. Two sliders may be attached via the attachment devices to form a slider assembly which can accommodate both of the user's hands or feet.

20 Claims, 4 Drawing Sheets

(51) Int. Cl.
*A61F 7/10* (2006.01)
*A61F 7/00* (2006.01)

(56) References Cited

U.S. PATENT DOCUMENTS

| | | | | |
|---|---|---|---|---|
| 5,551,173 | A * | 9/1996 | Chambers | A43B 7/146 |
| | | | | 36/141 |
| 5,891,002 | A * | 4/1999 | Maki | A63B 22/16 |
| | | | | 482/146 |
| 6,055,676 | A * | 5/2000 | Bainbridge | A41D 13/015 |
| | | | | 2/16 |
| D478,997 | S * | 8/2003 | Viner | D24/212 |
| 6,901,629 | B2 * | 6/2005 | Wurdack | A47B 91/002 |
| | | | | 16/42 R |
| D562,918 | S | 2/2008 | Tuller | |
| 7,811,216 | B2 * | 10/2010 | Babiarz | A63B 21/0085 |
| | | | | 446/220 |
| 7,882,568 | B2 * | 2/2011 | Fee | A41D 13/0562 |
| | | | | 2/24 |
| 8,105,218 | B1 * | 1/2012 | Vayntraub | A63B 23/1236 |
| | | | | 482/141 |
| 8,382,645 | B2 * | 2/2013 | Mylrea | A63B 21/0004 |
| | | | | 482/148 |
| 8,480,547 | B2 * | 7/2013 | Coates | A63B 21/00047 |
| | | | | 482/131 |
| 8,702,574 | B2 * | 4/2014 | Abranchess | A63B 21/0004 |
| | | | | 482/141 |
| 8,827,879 | B2 * | 9/2014 | Nicholas | A63B 21/0004 |
| | | | | 482/131 |
| 8,858,402 | B2 * | 10/2014 | Bruschke | A63B 22/20 |
| | | | | 482/123 |
| 9,011,294 | B2 * | 4/2015 | Mylrea | A63B 21/0004 |
| | | | | 482/51 |
| 9,028,382 | B2 * | 5/2015 | Chang | A63B 22/20 |
| | | | | 482/132 |
| 2001/0036885 | A1 * | 11/2001 | Castellot, Jr. | A63B 21/012 |
| | | | | 482/79 |
| 2005/0034268 | A1 * | 2/2005 | Wurdack | A47B 91/002 |
| | | | | 16/42 R |
| 2007/0186374 | A1 * | 8/2007 | Thaw | A47B 91/066 |
| | | | | 16/42 R |
| 2007/0287605 | A1 * | 12/2007 | Mylrea | A63B 21/0004 |
| | | | | 482/92 |
| 2008/0042025 | A1 * | 2/2008 | Brouard | A47B 91/06 |
| | | | | 248/188.9 |
| 2008/0176684 | A1 * | 7/2008 | Edwards | A63B 67/14 |
| | | | | 473/588 |
| 2008/0282438 | A1 * | 11/2008 | Boutaghou | A41D 13/0156 |
| | | | | 2/16 |
| 2009/0162596 | A1 * | 6/2009 | Rios | A43B 13/04 |
| | | | | 428/45 |
| 2009/0247378 | A1 * | 10/2009 | Carlesimo | A63B 21/00047 |
| | | | | 482/141 |
| 2011/0071441 | A1 * | 3/2011 | Rodgers | A61H 1/0266 |
| | | | | 601/5 |
| 2011/0230313 | A1 * | 9/2011 | Gamboa | A63B 22/20 |
| | | | | 482/51 |
| 2012/0244998 | A1 * | 9/2012 | Rao | A63B 71/0054 |
| | | | | 482/70 |
| 2015/0190668 | A1 * | 7/2015 | Ferdinandsen, II | A63B 21/012 |
| | | | | 482/93 |
| 2015/0238796 | A1 * | 8/2015 | Chang | A63B 22/20 |
| | | | | 482/114 |

* cited by examiner

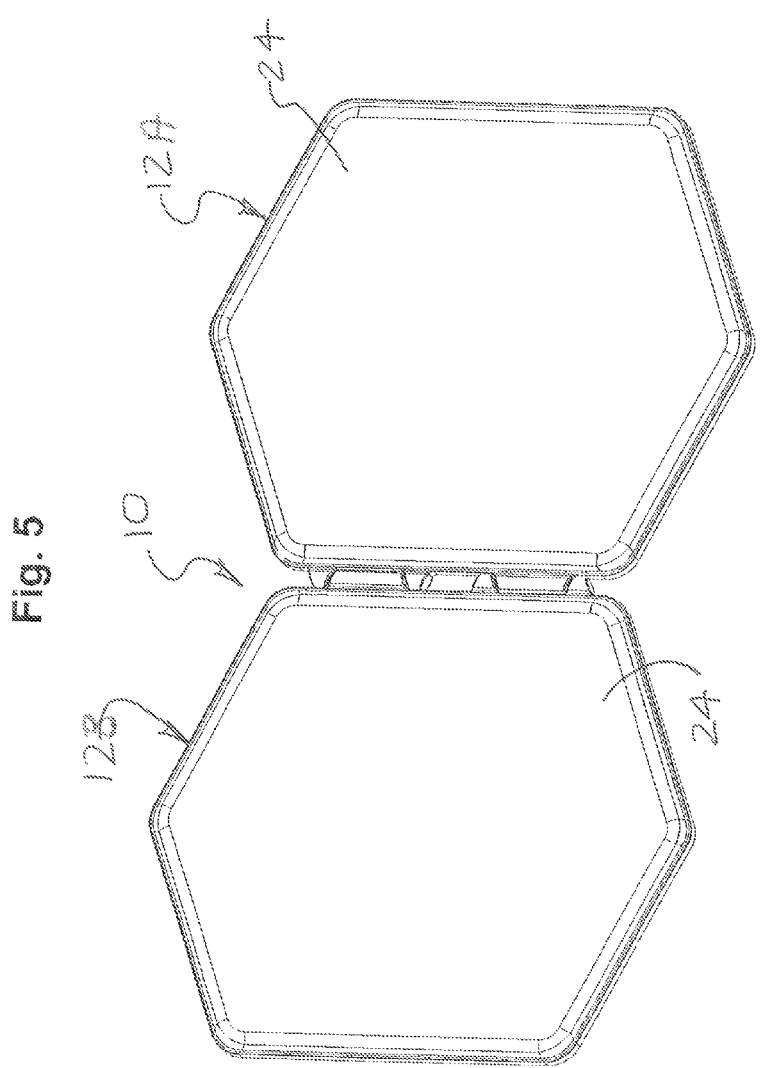
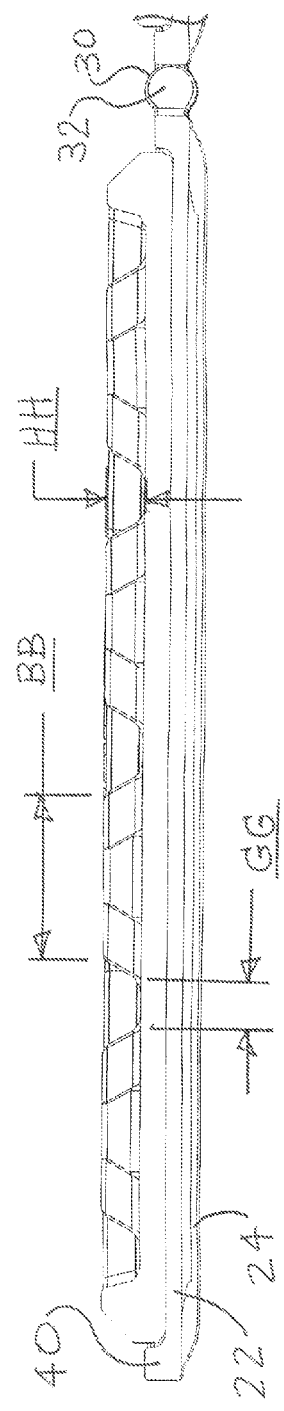
Fig. 5
Fig. 6

FLOOR EXERCISE SLIDER

PRIORITY CLAIM

This Application claims priority to U.S. Provisional Patent Application No. 61/939,553, filed Feb. 13, 2014 and incorporated herein by reference.

BACKGROUND OF THE INVENTION

Floor exercise sliders are pads or discs having a low-friction bottom surface. With the user's hands and/or feet on the pads, various exercises may be performed, with the sliders providing added intensity and resistance. Sliders are useful for exercising the arms, the legs and the core. Although various types of sliders have been used in the past, disadvantages remain with existing designs. Improved slider designs are needed.

SUMMARY OF THE INVENTION

A floor exercise slider may have an attachment device on a side of a frame. A resilient pad may be attached to an upper surface of the frame, with the resilient pad having raised blocks separated by grooves. A low friction slide plate may be joined to a bottom surface of the frame. The raised blocks may be evenly spaced apart laterally and/or longitudinally by the grooves. Two sliders may be attached via the attachment devices to form a slider assembly which can accommodate both of the user's hands or feet.

BRIEF DESCRIPTION OF THE DRAWINGS

FIG. 5 is a bottom perspective view of the slider assembly shown in FIG. 1.

FIG. 6 is a section view taken along line 6-6 of FIG. 4.

DETAILED DESCRIPTION OF THE DRAWINGS

Figure 1:
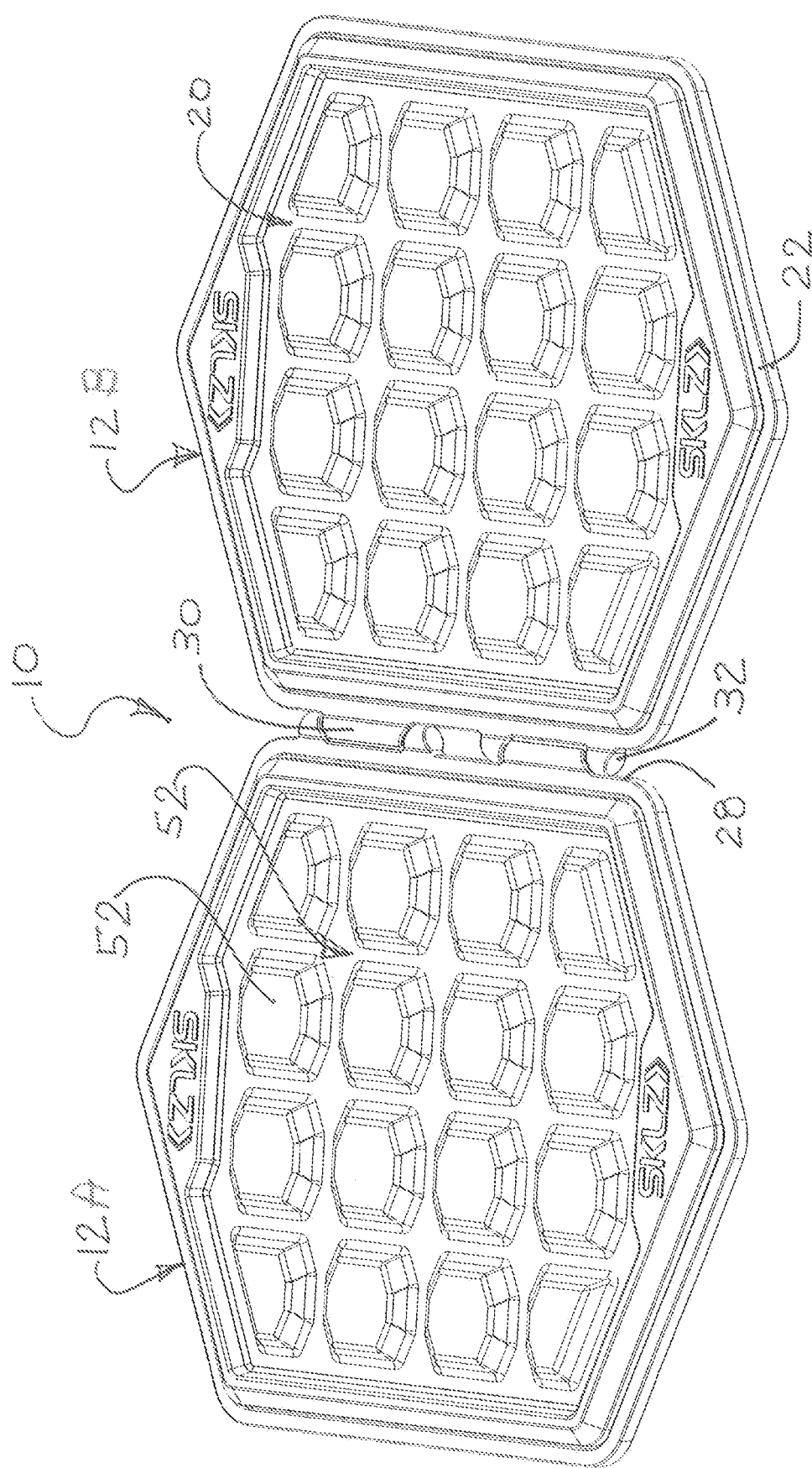
FIG. 1 is a top perspective view of two sliders attached to each other to form a slider assembly.
Figure 2:
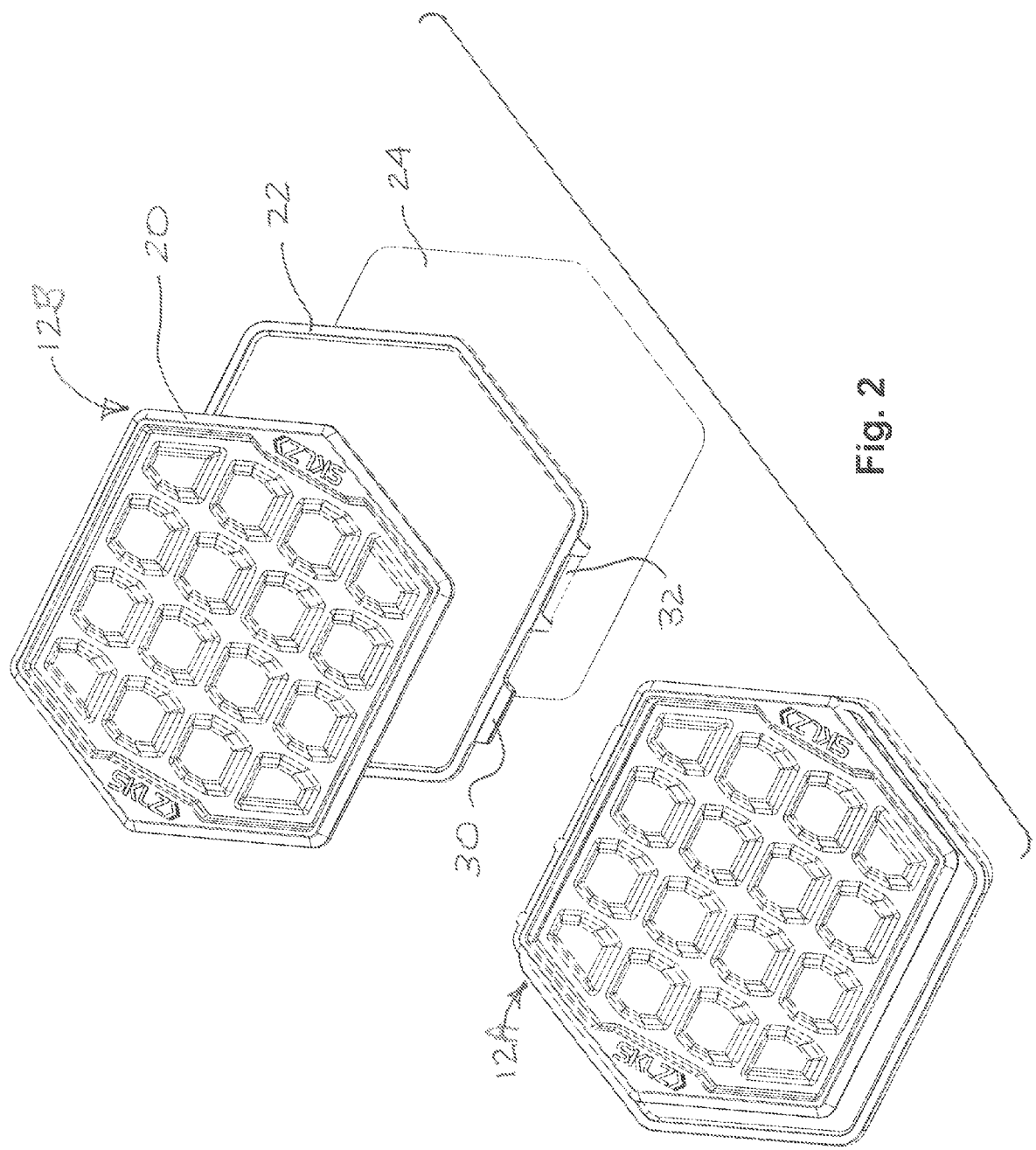
FIG. 2 is an exploded top perspective view of the slider assembly of FIG. 1.

As shown in FIG. 1, a slider assembly 10 includes a first slider 12A and a second slider 12B which may be attached to each other. The slider 12A may be identical to the slider 12B, with both sliders having the same size, shape and appearance. As shown in FIG. 2 the slider 12A (or 12B) has a resilient pad 20 attached to a frame or shell 22. The pad 20 may be rubber or plastic selected to provide a comfortable hand surface. The frame 22 may be a plastic or metal plate, optionally with a raised rim 40 around the perimeter, as shown in FIG. 6. The pad 20 is attached to the top surface of the frame 22 via adhesives, fasteners, or using other techniques. As shown in FIG. 2, a low friction bottom plate or layer 24 may be attached onto the bottom surface of the frame 22, to allow the slider 12A to easily slide over floor surfaces. In some designs the bottom plate 24 may be omitted with the slider simply sliding on the bottom surface of the frame.

Figure 4:
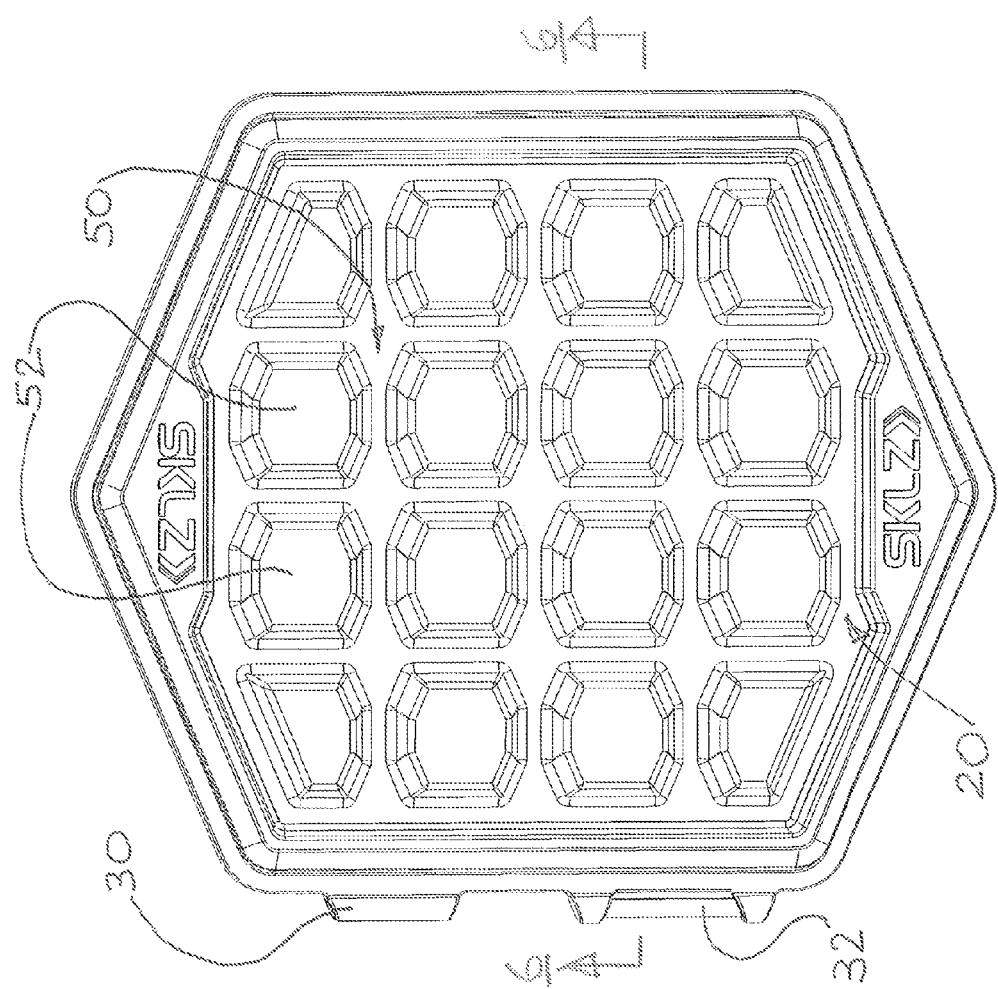
FIG. 4 is a plan view of either of the sliders shown in FIGS. 1-2.
Figure 3:
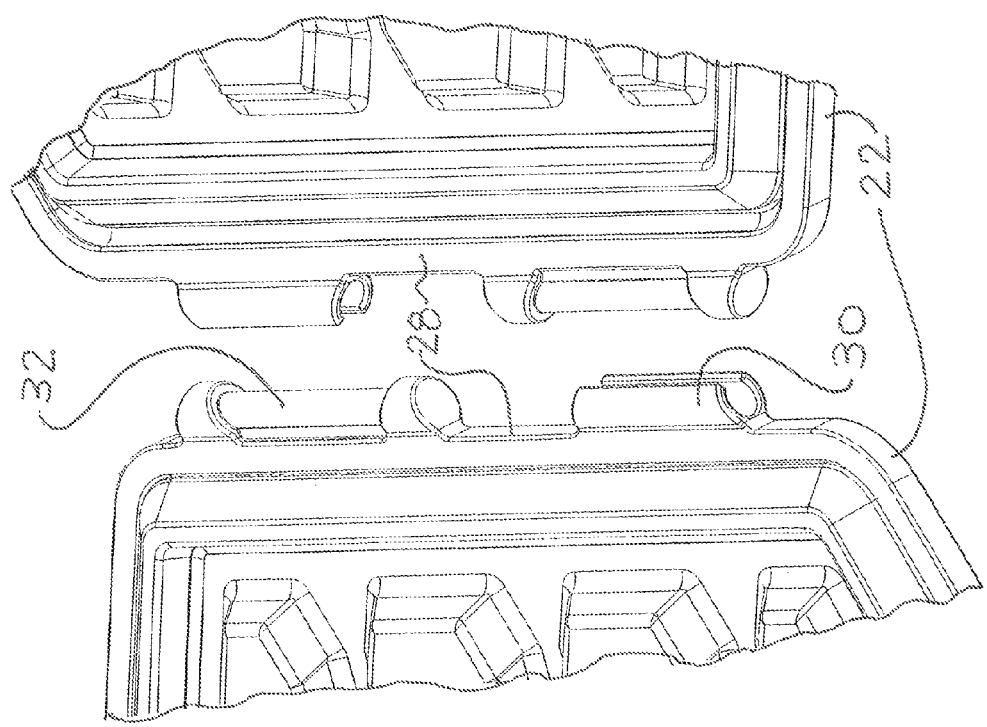
FIG. 3 is an enlarged perspective view of the attachment device of the sliders shown in FIGS. 1-12.

Turning to FIGS. 3 and 4, an attachment is provided on one edge or side of the frame 22 for attaching the slider 12A to another slider 12B. The attachment in the example shown includes a clip 30 which can snap onto a bar or pin 32 to form a hinge joint attachment. Various equivalent attachments may also be used including snaps, pins, tapes, hook and loop fasteners, rings, fasteners, etc., as the attachment need only act to hold the sliders together for use of the sliders as a slider assembly, while also allowing the sliders to be separated for use individually, regardless of the type of attachment used. The attachment shown is integral with the frame 22. However, attachments using additional separate pieces may also be used. For example, the attachment may be provided as hinge knuckles on the frame 22 with a separate hinge pin that may be inserted and removed to attach and separate the sliders. This and similar designs may allow the sliders to be folded flat against each other while attached.

As shown in FIG. 4, the slider 12A may be shaped as a polygon, such as a hexagon. The slider may also be shaped as a square or rectangle, a pentagon or an octagon. Curved shapes such as an oval, ellipse or circle may also be used. In the example of FIG. 4, the slider is a hexagon having two longer and four shorter sides. In this case the attachment may be provided on one of the longer sides 28.

Also as shown in FIG. 4, the pad 20 may include spaced apart raised blocks 52. The blocks 52 may be equally spaced apart in a pattern with lateral and longitudinal grooves 50 between the blocks, optionally forming a waffle iron type of pattern. Referring now also to FIG. 6, one or more of the blocks 52 may have sloped or angled sides extending from a floor of the pad at the grooves 50 to the top surface of the block 52. The block may have a flat top surface. The grooves 50 and sloped or angled sides of the blocks provide finger spaces between adjacent columns of blocks, with the top surfaces of the blocks spaced apart by 5 to 15 or 20 mm, and with the blocks having a width, diameter or major dimension (BB in FIG. 6) of 15 to 30 mm. The width of the grooves at the floor of the pad, shown as dimension GG in FIG. 6, may range from 3-15 or 5-12 mm, depending on other design parameters. The blocks 52 may have a height HH from the pad floor to the block top surface of 3-15 mm. The number of blocks used may vary with the size and shape of the pad 20. The example of FIG. 4 uses two complete rows and columns of four blocks each, for a total of 12 full blocks plus one partial block at each of the corners or vertices. Also as shown in FIG. 6, the pad 20 may be positioned within the rim 40 of the frame 22, with the top surfaces of the blocks 52 generally co-planer, +/−1-3 mm, with the top surface of the rim 40.

In use, the sliders 12A and 12B may be used separately to perform a wide range of floor exercises with the user placing the hands or feet onto the pads 20 and sliding the sliders on the floor. For some exercises, four sliders may be used to allow sliding movement of the hands and the feet. The blocks 52 and grooves 52 provide a comfortable and firm gripping surface via the user's fingers resting partially within one or more of the grooves.

The sliders 12A and 12B may be attached to each other to provide a single slider assembly large enough to accommodate both hands or both feet, to perform other types of sliding floor exercises. Two slider assemblies may be used with both hands on one slider assembly and both feet on the other slider assembly.

Thus, a novel slider has been shown and described. Various changes and substitutions may of course be made without departing from the spirit and scope of the invention. The invention, therefore, should not be limited except by the following claims and their equivalents.

The invention claimed is:

1. A floor exercise slider assembly, comprising:
a first slider including a first frame;
a first attachment device on a side of the first frame;
a first resilient pad attached to an upper surface of the first frame, with the first resilient pad having a first array of raised blocks separated by grooves;
a first slide plate formed on or attached to a lower surface of the first frame disposed opposite the upper surface of the first frame, with the first slide plate structurally configured to permit a sliding movement, and the first resilient pad is engageable with one or more of a hand and a foot of a user, when performing sliding floor exercises;
a second slider including a second frame;
a second attachment device on a side of the second frame;
a second resilient pad attached to an upper surface of the second frame, with the second resilient pad having a second array of raised blocks separated by grooves; and
a second slide plate formed on or attached to a lower surface of the second frame disposed opposite the upper surface of the second frame, with the second slide plate structurally configured to permit a sliding movement, and the second resilient pad is engageable with one or more of a hand and a foot of a user when performing sliding floor exercises,
with the first attachment device releasably attached to the second attachment device thereby releasably engaging the first slider with the second slider to form the floor exercise assembly, and with the first and second attachment devices forming a hinge.

2. The slider assembly of claim 1 wherein the first slider and the second slider have the same size and shape.

3. The slider assembly of claim 1 with the first slider and second slider each having a plurality of long sides and a plurality of short sides, and with the first attachment device on a long side of the first slider and with the second attachment device on a long side of the second slider.

4. The slider assembly of claim 1 with the grooves of the first and second resilient pads comprising lateral grooves, and with the lateral grooves of the first resilient pad aligned with the lateral grooves of the second resilient pad.

5. The slider assembly of claim 1 with the first slider pivotally attached to the second slider.

6. The slider assembly of claim 1 with a center of the first resilient pad spaced apart from a center of the second resilient pad by 10 to 30 cm.

7. The slider assembly of claim 1 with at least one of the first array of raised blocks and the second array of raised blocks evenly spaced apart.

8. The slider assembly of claim 1 with at least one of the first array of raised blocks and the second array of raised blocks separated by lateral grooves and by longitudinal grooves perpendicular to the lateral grooves.

9. The slider assembly of claim 1 with at least one of the first frame and the second frame comprising a hexagon having four equal length shorter sides, and two equal length longer sides.

10. The slider assembly of claim 1 with at least one of the first frame and the second frame comprising a plastic shell having a rim surrounding a pad recess, and with at least one of the first resilient pad and the second resilient pad positioned in the pad recess, and with a top surface of the rim substantially co-planer with a top surface of at least one of the first array of raised blocks and the second array of raised blocks.

11. A floor exercise slider assembly, comprising:
a first slider including a first frame;
a first attachment device on a side of the first frame;
a first resilient pad attached to an upper surface of the first frame, with the first resilient pad having a first array of raised blocks separated by grooves;
a first slide plate formed on or attached to a lower surface of the first frame disposed opposite the upper surface of the first frame, with the first slide plate structurally configured to permit a sliding movement, and the first resilient pad is engageable with one or more of a hand and a foot of a user, when performing sliding floor exercises;
a second slider including a second frame;
a second attachment device on a side of the second frame;
a second resilient pad attached to an upper surface of the second frame, with the second resilient pad having a second array of raised blocks separated by grooves; and
a second slide plate formed on or attached to a lower surface of the second frame disposed opposite the upper surface of the second frame, with the second slide plate structurally configured to permit a sliding movement, and the second resilient pad is engageable with one or more of a hand and a foot of a user, when performing sliding floor exercises,
with the first attachment device releasably attached to the second attachment device thereby releasably engaging the first slider with the second slider to form the floor exercise assembly, and with the first slider pivotally attached to the second slider.

12. The slider assembly of claim 11 with the first and second attachment devices forming a hinge.

13. The slider assembly of claim 11 wherein the first slider and the second slider have the same size and shape.

14. The slider assembly of claim 11 with the first slider and second slider each having a plurality of long sides and a plurality of short sides, and with the first attachment device on a long side of the first slider and with the second attachment device on a long side of the second slider.

15. The slider assembly of claim 11 with the grooves of the first and second resilient pads comprising lateral grooves, and with the lateral grooves of the first resilient pad aligned with the lateral grooves of the second resilient pad.

16. The slider assembly of claim 11 with a center of the first resilient pad spaced apart from a center of the second resilient pad by 10 to 30 cm.

17. The slider assembly of claim 11 with at least one of the first array of raised blocks and the second array of raised blocks evenly spaced apart.

18. The slider assembly of claim 11 with at least one of the first array of raised blocks and the second array of raised blocks separated by lateral grooves and by longitudinal grooves perpendicular to the lateral grooves.

19. The slider assembly of claim 11 with at least one of the first frame and the second frame comprising a hexagon having four equal length shorter sides, and two equal length longer sides.

20. The slider assembly of claim 11 with at least one of the first frame and the second frame comprising a plastic shell having a rim surrounding a pad recess, and with at least one of the first resilient pad and the second resilient pad positioned in the pad recess, and with a top surface of the rim substantially co-planer with a top surface of at least one of the first array of raised blocks and the second array of raised blocks.

* * * * *